United States Patent [19]
Puri et al.

[11] Patent Number: 6,089,100
[45] Date of Patent: Jul. 18, 2000

[54] REAL-TIME SPATIAL PARTICULATE MASS DEPOSITION TESTER

[75] Inventors: Virendra M. Puri; Premdeep S. Dhanoa, both of State College, Pa.

[73] Assignee: The Penn State Research Foundation, University Park, Pa.

[21] Appl. No.: 09/130,407

[22] Filed: Aug. 6, 1998

Related U.S. Application Data

[60] Provisional application No. 60/054,981, Aug. 6, 1997.

[51] Int. Cl.$^7$ ...................................................... G01N 3/00
[52] U.S. Cl. ............................................................. 73/788
[58] Field of Search ............................. 73/818, 819, 821, 73/824, 825, 790, 788, 803

[56] References Cited

U.S. PATENT DOCUMENTS

| | | | |
|---|---|---|---|
| 3,786,645 | 1/1974 | Cann | 62/605 |
| 3,794,215 | 2/1974 | Osterhaus | 222/1 |
| 3,972,686 | 8/1976 | Johnson et al. | |
| 4,039,431 | 8/1977 | Baillie | |
| 4,182,383 | 1/1980 | Adomitis et al. | 141/5 |
| 4,234,049 | 11/1980 | Oliver | 177/105 |

(List continued on next page.)

OTHER PUBLICATIONS

Aoki, "Stresses of powders and granular materials in bins and hoppers," Theoretical and Applied Mechanics, p. 9–24, (Jun. 11, 1976).

Bocchini, "Influence of small die width on filling and compacting densities," Powder Metallurgy, vol. 30 (No. 4), p. 261–266, (Jun. 11, 1987).

Coshell, "X–ray computed tomography of Australian oil shales:non–destructive visualization and density determination," Fuel, vol. 73 (No. 8), p. 1317–1321, (Jun. 11, 1994).

Faikin, "Influence of the rate of die filling on the density of the powder," Soviet Powder Metallurgy and Metal Ceramics, vol. 15 (No. 8), p. 590–592, (Jun. 11, 1976).

Hosseini–Ashrafi, "Tomographic study of voidage profiles in axially symmetric granular flows," Chemical Engineering Science, Pregamon Press Ltd, vol. 48 (No. 1), p. 53–67, (Jun. 11, 1993).

Kantzas, "Computation of holdups in fluidized and trickle beds by computer–assisted tomography," AIChE Journal, vol. 40 (No. 7), p. 1254–1261, (Jul. 11, 1994).

Kondoh, "Visualization of powder behavoir for gravity filling," Toyota Cental R&D Labs, Inc., (Jun. 11, 1996).

Kwade, "Determination of the stress Ratio in Uniaxial Compresion Tests, Part 1," Powder handling and Processing, vol. 6 (No. 1), p. 61–65, (Jun. 11, 1994).

Molenda, "Effect of filling method on load distribution in model grain bins," ASAE Paper No. 94–4517, p. 1–14, (Jun. 11, 1994).

Moriyama, "Effect of filling methods on the wall pressure near the transition in a bin," Bulk Solids Handling, vol. 5 (No. 3), p. 603–609, (Jun. 11, 1985).

Moysey, "The effect of grain spreaders on grain friction and bin wall pressures," J. Agric. Engng. Res., p. 149–156, (Jun. 11, 1984).

Munch–Anderson, "Size Effects in slender grain silos," Bulk Solids Handling, vol. 6 (No. 5), p. 885–889, (Jun. 11, 1986).

Nielsen, "Load distribution in silos influenced by anisotropic grain behavior," Intl. Conf. onbulk Materials Storage, Handling and Transportation, p. 5 pages, (Jun. 11, 1983).

(List continued on next page.)

*Primary Examiner*—Max Noori
*Attorney, Agent, or Firm*—Thomas J. Monahan

[57] ABSTRACT

The present invention is a real-time spatial particulate mass deposition tester. The tester is based on the principle that an anisotropic fill density distribution would result in an uneven particulate vertical pressure distribution on the inside face of the bottom surface of the die. Further, this uneven particulate vertical pressure distribution can be detected by placing multiple, sufficiently sensitive load cells on the inside surface at the bottom of the die, and analyzing the output signals acquired from the load cells using any suitable data acquisition system.

7 Claims, 7 Drawing Sheets

U.S. PATENT DOCUMENTS

| | | | |
|---|---|---|---|
| 4,794,799 | 1/1989 | Paakkinen | 73/803 |
| 5,476,631 | 12/1995 | Brown et al. | 419/38 |

OTHER PUBLICATIONS

Phogat, "Simultaneous measurement of the spatial distribution of soil water content and bulk density," Soil Science Society of America Journal, vol. 55 (No. 4), p. 908–915, (Jun. 11, 1991).

Readey, "Compaction of spray–dried ceramic powders: an experimental study of the factors that control green density," International Sample Technical Conf., p. 622–634, (Jun. 11, 1995).

Smid, "Effect of filling method on the packing distrubution of a catalyst bed", Chem. Eng. Technol. vol. 16, p. 114–118 (1993).

Tollner, "Relating x–ray absorption to density and water content in apples", Transaction of the ASAE, vol. 35 (No. 6), p.1921–1928 (1992).

RANGE: 0-50 gm.
REPEATABILITY: +- 0.1% F.S.
HYSTERISIS: +- 0.5% F.S.

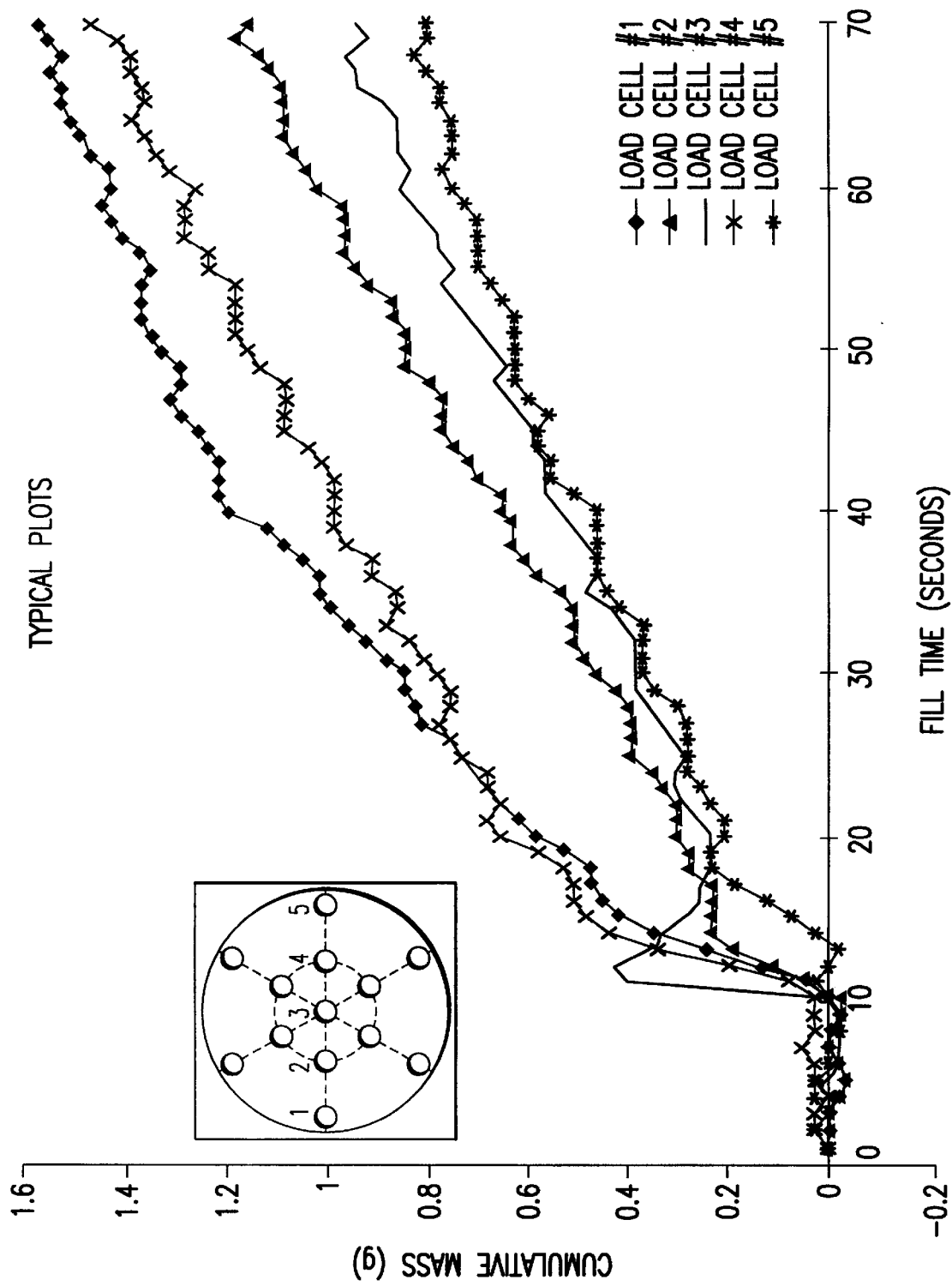

REAL-TIME SPATIAL PARTICULATE MASS DEPOSITION TESTER

This application claims priority to U.S. Provisional Application Ser. No. 60/054,981 filed Aug. 6, 1997, which is herein incorporated by reference.

BACKGROUND OF THE INVENTION

A wide variety of products such as feed pellets, tablets, tool inserts, electronic components and automobile parts are produced by pouring a fixed mass or volume of dry cohesive particulate material into a die and subjecting the material to high pressures. This manufacturing technique is referred to as compaction or pelletization and the pressed part is referred to as compact. The quality of the product made by pelletizing is recognized to be dependent upon many factors such as intrinsic material properties, particulate material properties, nature of applied load, and die geometry. Many pelletization defects such as lamination, capping, and stress cracking etc. are caused by anisotropic compaction of the particulate material. It is further recognized by researchers that the anisotropic compaction, among other factors, is attributable to non-uniform pre-compaction fill-density of the particulate material in the die. Filling or the deposition of powders in confined spaces such as dies is the required first step in the process of manufacturing pressed parts/products. Since errors are usually compounded in any manufacturing process, it stands to reason that ensuring a pre-compaction uniform particulate deposition in the die or mold would be an effective method of ensuring and enhancing quality of the pressed compacts.

Even though researchers have studied the effect of filling methods on fundamental particulate properties and load distribution in large storage systems, there exists a significant lack of qualitative and quantitative analysis of the process of die filling in relation to a particulate material's pre-compaction density distribution within the die volume. The ability to measure the in-situ, pre-compaction fill density distribution within the particulate mass inside the die volume is of paramount importance to the objectives of research work and no study is believed to exist where researchers have carried out such an in-situ density distribution of particulates in dies or molds. Five potential techniques currently available are radiogaging, x-ray CAT scanning, Process Tomography, vacuum assisted epoxy impregnation and magnetic resonance imaging (MRI), A pros and cons analysis involved weighing the financial viability verse the technical limitations of the different techniques found that none of these techniques were a feasible option. For example, a sample of wheat flour was tested for its spatial density distribution in a CAT scan machine. While the results were promising, the costs involved were considered unacceptable on account of the fact that the CAT scan machine is very expensive to own or rent. Even if unlimited funds were available to do CAT scanning, it would simply be impossible to test certain powders that would cause high attenuation of incident x-rays so as to render them undetectable by the CAT scan sensors. Similarly, while a MRI machine can do extensive imaging of the human body, test results on a sample of wheat flour tested in a MRI machine were found to be negative. Even if a MRI machine could be coupled to detect the presence of a certain molecule in a given powder, the prohibitive costs of MRI machines (even costlier than CAT scan machines) would preclude their use. The radio-gaging and process tomography techniques involve similar high ownership or rental costs. The vacuum assisted epoxy impregnation technique is an inexpensive technique, but its use in achieving the objectives of this study were considered unacceptable for two reasons. The first reason being that percolation effects of epoxy through the powder mass may cause particle dislocation. The second reason being that there could be potential chemical reactions between the epoxy and particulate material.

It is an object of the present invention to provide a test apparatus to determine spatial, in-situ fill density distribution of a material in confined spaces.

It is an object of the present invention to provide a test apparatus to allow the determination of the effect of filling methods, rate of fill, die cross-section and die size (aspect ratio) on the spatial fill density distribution of a material within a die volume.

SUMMARY OF THE INVENTION

The present invention is a real-time spatial particulate mass deposition tester including a lower plate acting as a base; a middle plate mounted to the lower plate; the middle plate including at least one load cell extending upward from the middle plate and at least one wire pathway for wiring of the load cell; and an upper plate mounted to the middle plate, the upper plate including at least one through hole to receive the load cells which extends from the middle plate. The mass deposition tester further includes a least one dowel extending upward from the lower plate and at least one dowel hole in each of the middle plate and upper plate to receive the dowel. Also the present invention provides a method of measuring the deposition of a material in an open ended die. The method is placing the open ended die on a tester including a lower plate acting as a base, a middle plate mounted to the lower plate, the middle plate including at least one load cell extending upward from the middle plate and at least one wire pathway for wiring of the load cell; and an upper plate mounted to the middle plate, the upper plate including at least one through hole to receive the load cell which extends from the middle plate; pouring the material into the die; recording the values produced by the load cell during pouring of the material.

BRIEF DESCRIPTION OF THE DRAWINGS

FIG. 7 is plot of recorded output data from the load cells of a prototype tester according to the present invention.

DETAILED DESCRIPTION OF THE INVENTION

The present invention is a real-time spatial particulate mass deposition tester. The tester is based on the principle that an anisotropic fill density distribution would result in an uneven particulate vertical pressure distribution on the inside face of the bottom surface of the die. Further, this uneven particulate vertical pressure distribution can be detected by placing multiple, sufficiently sensitive load cells on the inside surface at the bottom of the die, and analyzing the output signals acquired from the load cells using any suitable data acquisition system.

Figure 1A:
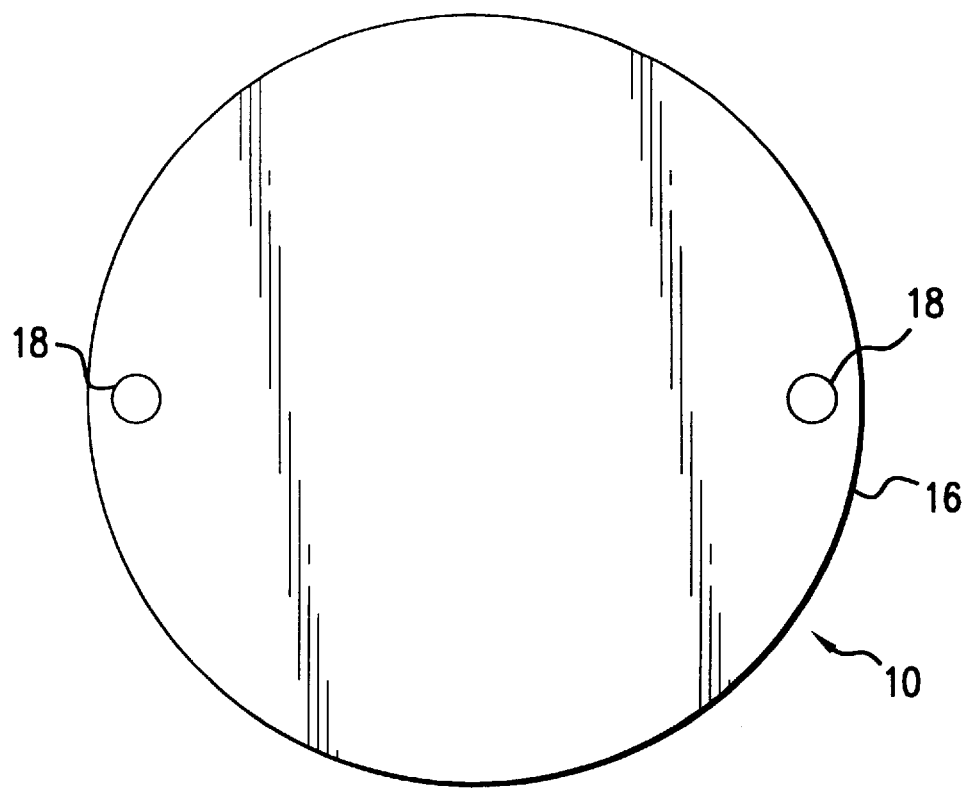
FIG. 1 is a top and side view of the real-time spatial particulate mass deposition tester according to the present invention.
Figure 1B:
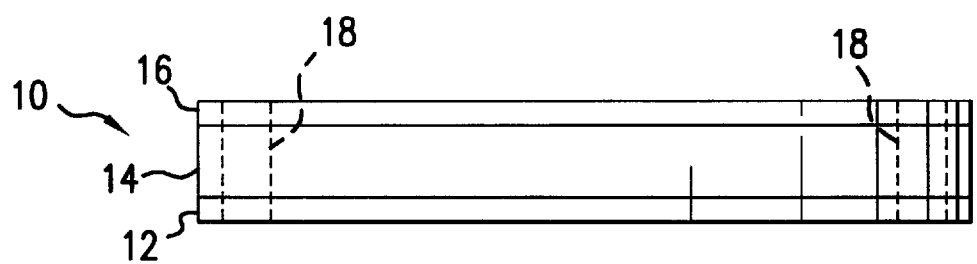
Figure 2A:
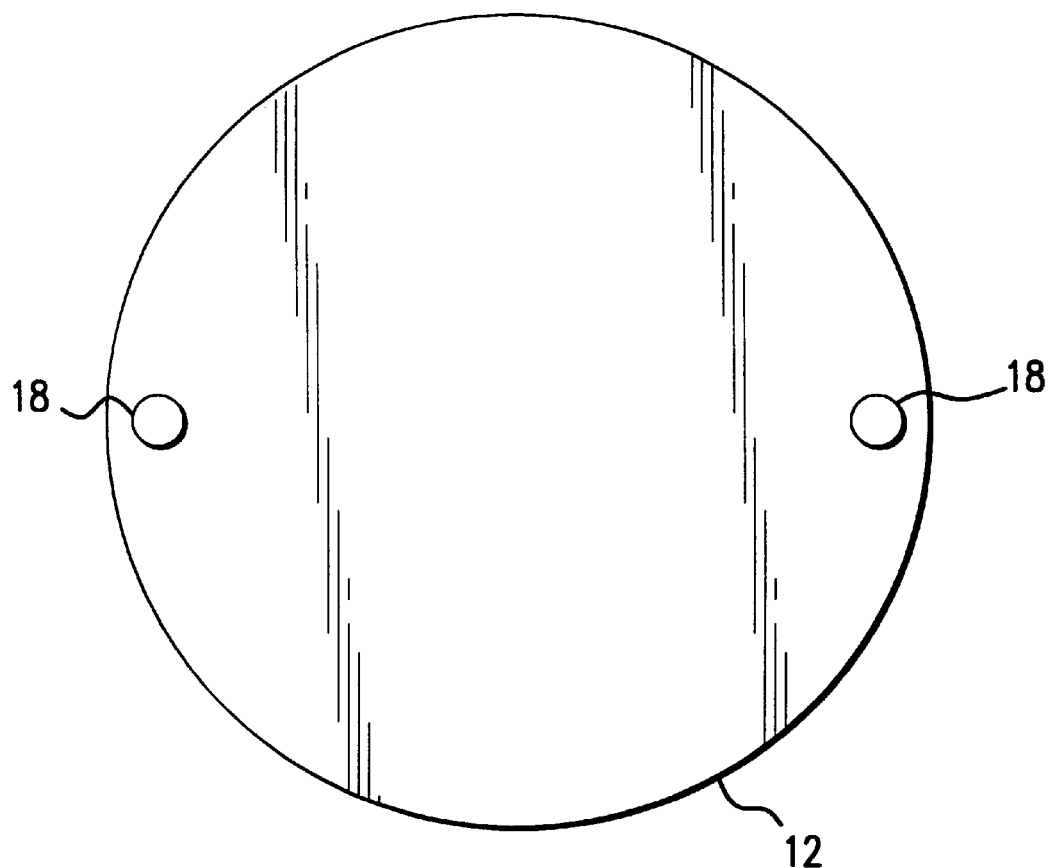
FIG. 2 is a top and side view of a lower plate according to the present invention.
Figure 2B:
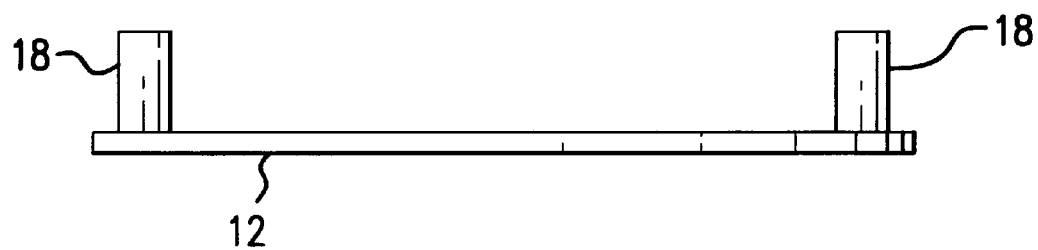
Figure 3A:
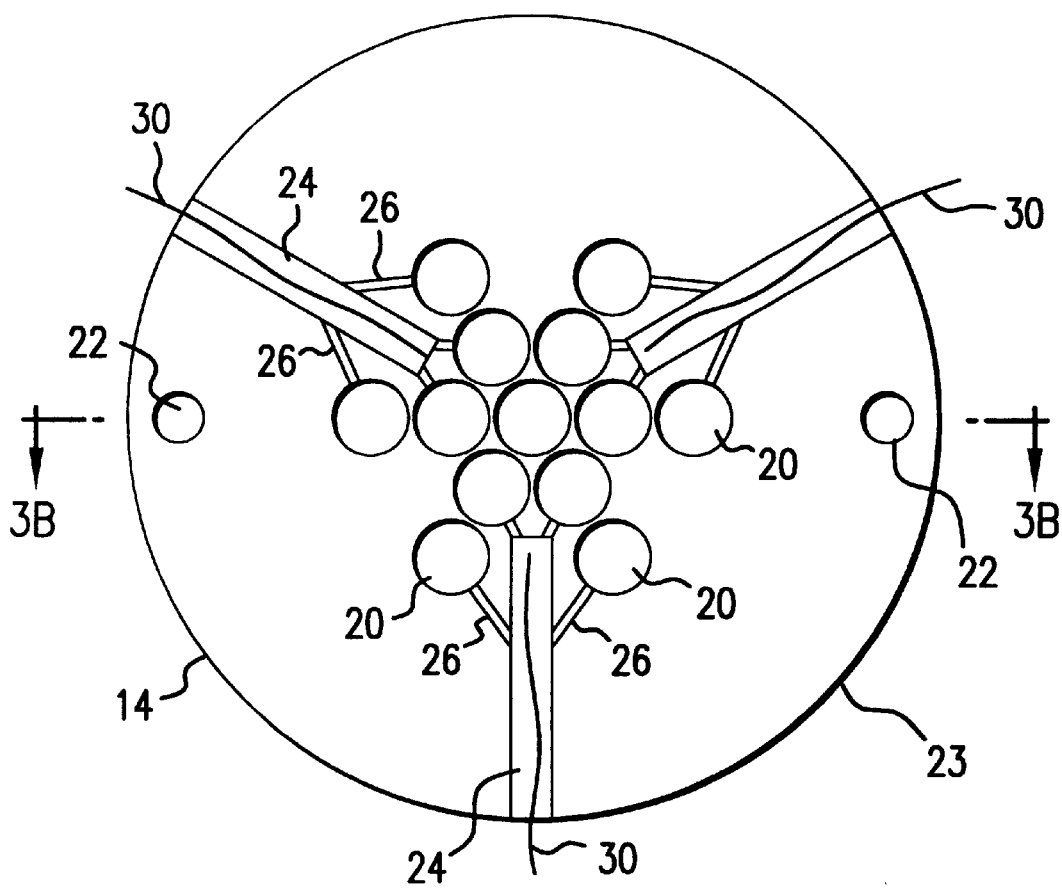
FIG. 3 is a top and side view of a middle plate according to the present invention.
Figure 3B:
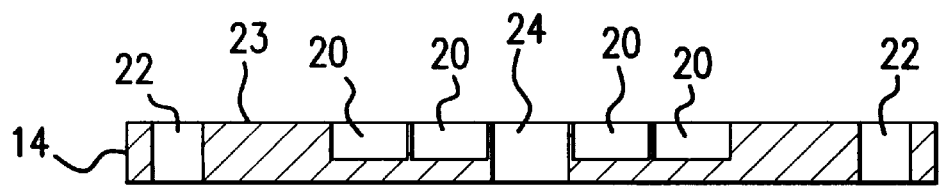

The tester 10 includes three circular stainless steel plates, lower plate 12, middle plate 14, and upper plate 16 respectively, which when assembled together result in a composite disc, as shown in FIG. 1. FIG. 2 shows the lower plate 12 with dowels 18 functioning as a base to hold the tester 10 together as one unit. FIG. 3 shows the middle plate 14 which includes blind holes 20, dowel holes 22, main channels 24 and secondary channels 26. Load cells 28 are embedded in place, with the help of snap rings (not shown), in the blind holes 20 which are drilled on a top surface 23 of the middle plate 14. Since the load cells 28 are removable, it is possible to change the configuration of placement of load cells 28 on the middle plate 14 as required for different experimental analysis purposes.

The FIG. 3 shows one possible configuration of blind holes 20 in the middle plate 14. The size of the plates 12,14 and 16 are varied depending upon the dimensions of the load cells 28 and the desired pattern of placement of load cells 28 on the middle plate 14. The dowel holes 22 of the middle plate 14 allow for placing of the middle plate 14 on the lower plate 12, whereby the dowels 18 are inserted into the dowel holes 22. The dowels 18 prevent movement of the middle plate 14 in relation to the lower plate 12 and upper plate 16. The secondary channels 26 connect to the main channels 24, thereby providing pathways for the wire 30 needed for the load cells 28.

Figure 4A:
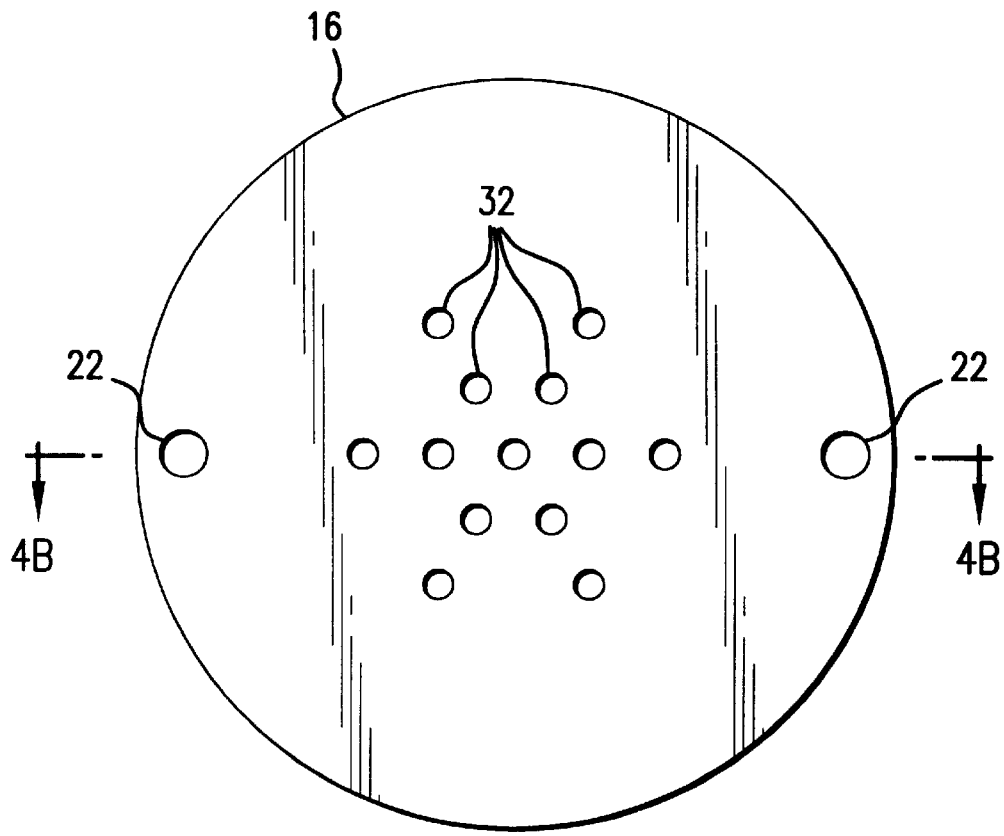
FIG. 4 is a top and side view of an upper plate according to the present invention.
Figure 4B:
Figure 5:
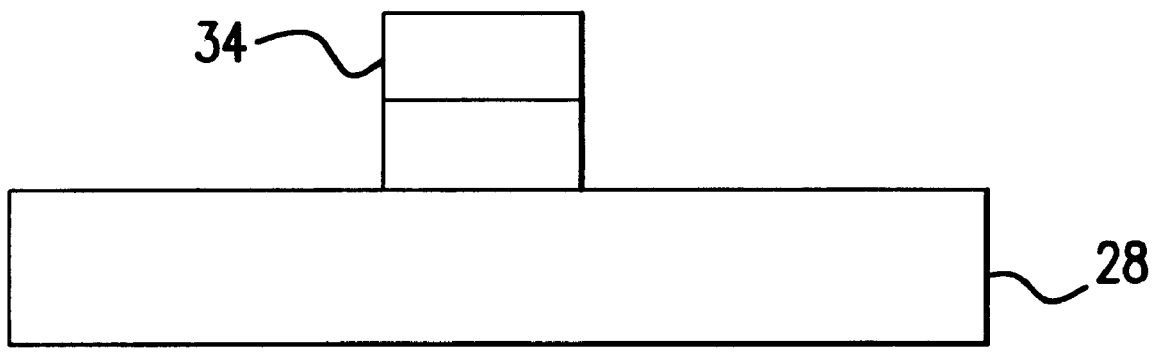
FIG. 5 is a schematic of the middle plate with a load cell according to the present invention.

FIG. 4 shows the upper plate 16 which functions as a rigid cover plate and serves to isolate the fill particulate material from the load cells 28. The upper plate 16 includes dowel holes 22 and through holes 32. The dowel holes 22 allow placement of the upper plate 16 on the middle plate 14 using the dowels 18 in the same manner as the middle plate 14 is placed on the lower plate 12. The through holes 32 correspond to the placement of the load cells 28 on the middle plate 14. The function of the through holes 32 is to allow extensions 34 on top of buttons (not shown) of the load cells 28 to measure vertical loads, as shown in FIG. 5. FIG. 5 shows the schematic of a button type electrical strain gage load cell 28 extending upward from the middle plate 14 and equipped with a small metallic cylindrical piece acting as an extension 34. The extension 34 is affixed with epoxy to the top of the button of the load cell 28. The thickness of this cylindrical piece is the same as the load cell button diameter and its height is such that the top surface of the extension 34 is flush with or slightly above a top surface 35 of the upper plate 16 when the upper plate 16 is placed on the middle plate 14. Whereby, the extensions 34 pass through the through holes 32 drilled in the upper plate 16.

Figure 6:
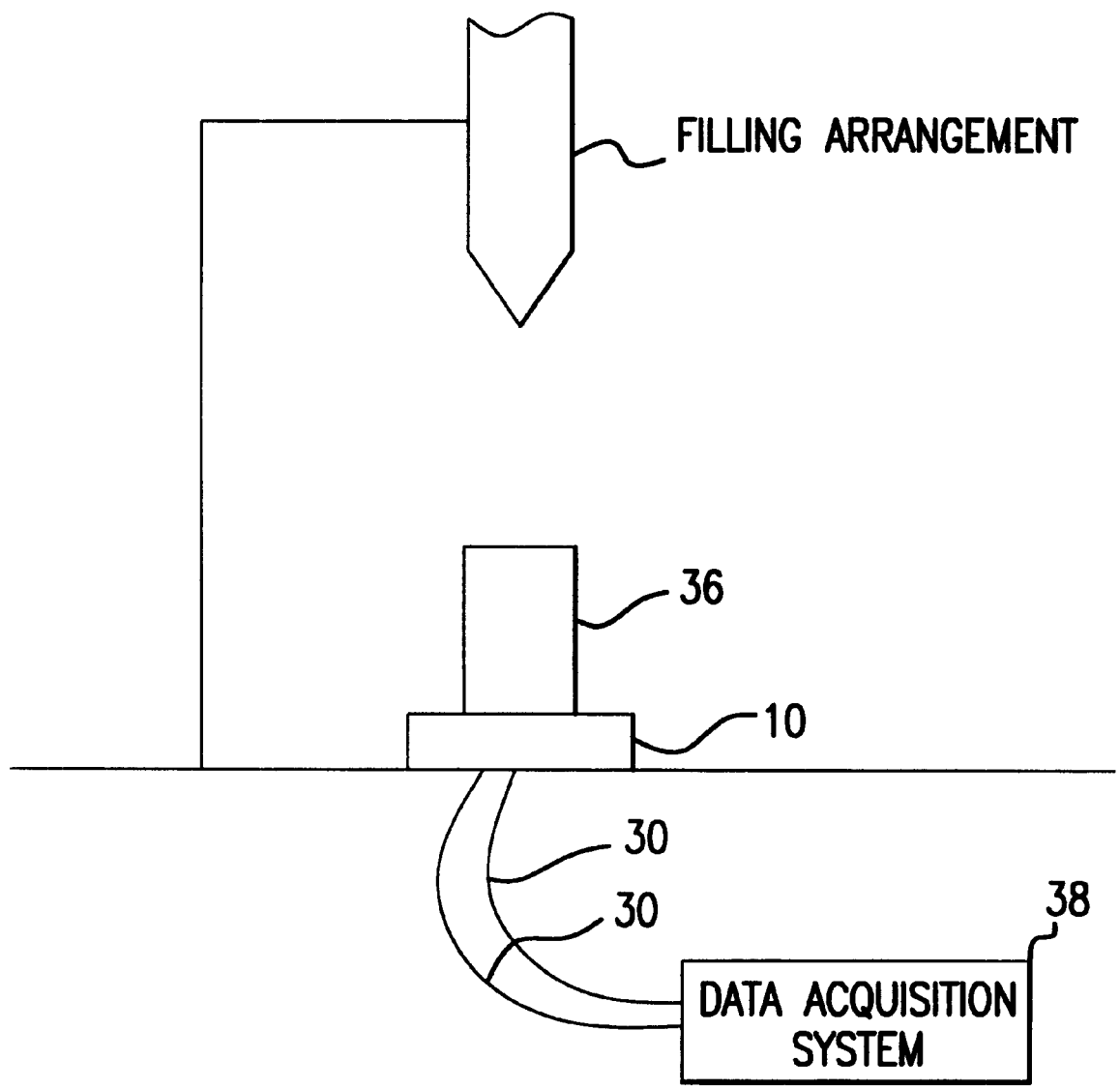
FIG. 6 is a schematic of the tester, die and data acquisition system according to the present invention.

FIG. 6 shows the schematic of the operation of the tester 10. The tester 10 is placed on a level horizontal surface. A thin plastic film (not shown) is placed over the tester 10 to isolate the fill particulate material from the upper plate 16 and the extensions 34 of load cells 28. An open-ended die 36 is then placed over the tester 10. The output voltage signal from load cells 28 is recorded using any suitable data acquisition system 38. The data acquisition system 38 is switched on and the fill particulate material is poured into the die 36 via any desired filling method. The resultant data captured by the data acquisition system 38 is then subjected to statistical analysis to determine the fill density distribution.

FIG. 7 shows plots of the typical output signals obtained from individual load cells of a prototype tester as the die filling process is carried out. The prototype tester measured 4 inches in diameter and was 0.625 inches thick. The layout of the load cells was a shown in FIG. 7 and the dimensions of blind holes correspond to Sensotec Inc. Model 13 sub- miniature load cells that were used with the prototype. The plots shown in FIG. 7 reflect a distinguishing, core feature of the tester, namely, its ability to not only determine the final mass accumulation at different locations along the bottom of the die but to also capture real-time data even as the die filling process is going on. An excellent example of the this feature is exhibited in the plot for load cell #3 in FIG. 7. To obtain the plots for FIG. 7, a clear acrylic pipe of 2 inch internal diameter was used as an open-ended cylindrical die and filled with a cohesionless Titanium Carbide powder using a funnel to deposit the material along the cylinder's axis from a height of 8.5 inches. Thus, load cell #3, located at the center of the bottom of the die, would experience an impact loading at the start of the die filling process (at the 10th second). This is clearly seen in the plot for load cell #3. Further, the undulating nature of the individual plots indicates the flow, the successive stages of formation and deformation of the heaped particulate as it fills the die. These plots also reveal that the accumulated mass above the load cells along the bottom of the die is not symmetrical with respect to the center.

While different embodiments of the invention have been described in detail herein, it will be appreciated by those skilled in the art that various modifications and alternatives to the embodiments could be developed in light of the overall teachings of the disclosure. Accordingly, the particular arrangements are illustrative only and are not limiting as to the scope of the invention which is to be given the full breadth of the appended claims and any and all equivalents thereof.

We claim:

1. A mass deposition tester comprising:
   a lower plate acting as a base;
   a middle plate mounted to said lower plate;
   said middle plate including at least one load cell extending upward from said middle plate and at least one wire pathway for wiring of said load cell; and
   an upper plate mounted to said middle plate, said upper plate including at least one through hole to receive said load cells which extends from said middle plate.

2. The mass deposition tester of claim 1, further including a least one dowel extending upward from said lower plate and at least one dowel hole in each of the middle plate and upper plate to receive said dowel.

3. The mass deposition tester of claim 1, wherein said middle plate further includes a blind hole in a top surface of the middle plate to receive said load cell.

4. The mass deposition tester of claim 1, further including at least one secondary channel leading from said load cell to a main channel to provide said wire pathway.

5. The mass deposition tester of claim 1, further including a data acquisition system connected to said load cell.

6. The method of measuring the deposition of a material in an open ended die comprising:
   a. placing said open ended die on a tester including a lower plate acting as a base, a middle plate mounted to said lower plate, said middle plate including at least one load cell extending upward from said middle plate and at least one wire pathway for wiring of said load cell; and an upper plate mounted to said middle plate, said upper plate including at least one through hole to receive said load cell which extends from said middle plate;
   b. pouring said material into said die;
   c. recording the values produced by said load cell during pouring of said material.

7. The method of claim 6, further including determining accumulated mass of said die from said recorded values.

* * * * *